United States Patent [19]

Ostrovskaya et al.

[11] 4,143,049
[45] Mar. 6, 1979

[54] METHOD FOR PREPARING 2H-TETRAZOLIUM CHLORIDE AND 2H-TETRAZOLIUM CHLORIDE HYDROCHLORIDE

[76] Inventors: Vera M. Ostrovskaya, Izumrudnaya ulitsa, 24, korpus 2, kv. 31; Olga T. Lushina, Komsomolsky prospekt, 5/2, kv. 33; Vladimir M. Dziomko, Boitsovaya ulitsa, 21, korpus 1, kv. 75; Julia A. Davydovskaya, Sevanskaya ulitsa, 21, korpus 1, kv. 35, all of Moscow, U.S.S.R.

[21] Appl. No.: 747,617

[22] Filed: Dec. 6, 1976

[51] Int. Cl.² .................. C07D 257/04; A01N 9/12
[52] U.S. Cl. ......................................... 260/308 D
[58] Field of Search ............................. 260/308 D

[56] References Cited
U.S. PATENT DOCUMENTS 2,713,581   7/1955   Pannone et al. ............... 260/308 D

OTHER PUBLICATIONS

Nineham, "The Chemistry of Formazans and Tetrazolium Salts", *Chem. Reviews*, 55, pp. 403–405 (1955).

*Primary Examiner*—Jose Tovar
*Assistant Examiner*—D. B. Springer
*Attorney, Agent, or Firm*—Lackenbach, Lilling & Siegel

[57] ABSTRACT

A method for preparing 2H-tetrazolium chloride hydrochlorides having the general formula

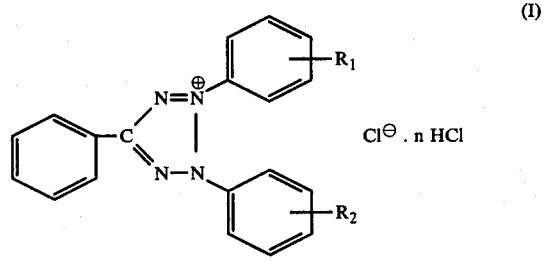

(I)

where $R_1$ and $R_2$ are H, OH, $NO_2$, Cl, or $OCH_2COOH$, and $n$ is from 0 to 3, and also di-2H-tetrazolium chloride hydrochloride having the formula

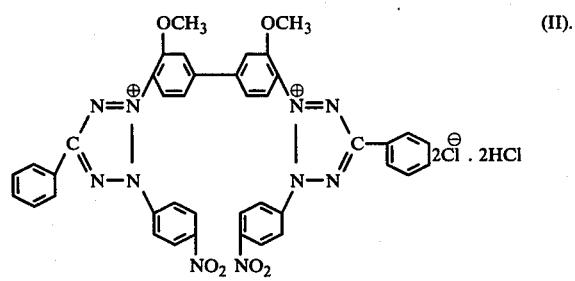

(II).

wherein the corresponding formazans are oxidized with chlorine in a medium of a polar organic solvent at a temperature from −5° to +20° C.

6 Claims, No Drawings

METHOD FOR PREPARING 2H-TETRAZOLIUM CHLORIDE AND 2H-TETRAZOLIUM CHLORIDE HYDROCHLORIDE

The invention relates to the methods of preparing 2H-tetrazolium salts, and more particularly 2H-tetrazolium chloride and 2H-tetrazolium chloride hydrochloride. Said salts are used in biochemistry and agrochemistry for studying the enzymes of the oxidation-reduction metabolism, of the dehydrogenase type in plant tissues, the eye lens, cell cultures, blood cells, blood serum, tumors, bacteria, salmonellae causing abdominal fever and mouse typhoid, animal organs, and in soil and effluents. Moreover, said salts are used in the germination and viability tests for the seeds of cotton, corn, wheat, etc., for the determination of boron hydrides in air, and also for histochemical studies of corn.

Known in the prior art are the methods for preparing 2H-tetrazolium salts by oxidizing formazans with lead tetraacetate, alkyl nitrites with acids, and yellow mercuric oxide, with subsequent isolation of the end product.

The disadvantages inherent in these methods are toxicity of the oxidants used (that persists in the end products) and relatively high cost of these oxidants.

Known also in the prior art is the method for preparing 2H-tetrazolium chlorides by oxidizing formazans at a temperature of 20°–100° C. in an aqueous medium in the presence of an organic solvent and a mixture of manganese dioxide and hydrochloride that react with the formation of chlorine, which in turn, oxidizes formazans. The obtained product is isolated from the reaction mixture by separating the aqueous phase from the organic one, by treating it with activated carbon, filtering, evaporating the filtrate, and purifying the end product by the known methods, e.g. by re-crystallization.

The disadvantages of this method are the low yield of the end product (32 percent) and the long duration of the oxidation reaction (at least 10 hours).

The object of this invention is to provide a method for preparing 2H-tetrazolium chlorides that would ensure higher yields and reduce the duration of the synthesis.

In accordance with these and other objects, the invention consists in a method for preparing 2H-tetrazolium chloride and 2H-tetrazolium chloride hydrochloride having the general formula

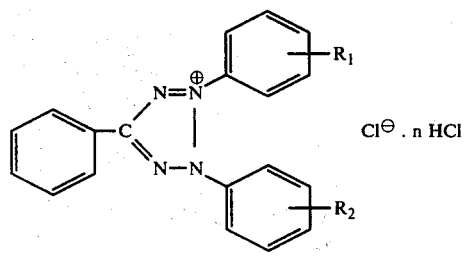

where $R_1$ and $R_2$ are H, OH, $NO_2$, Cl, or $OCH_2COOH$, and n is from 0 to 3, or 2H-tetrazolium chloride tetrachloride having the general formula

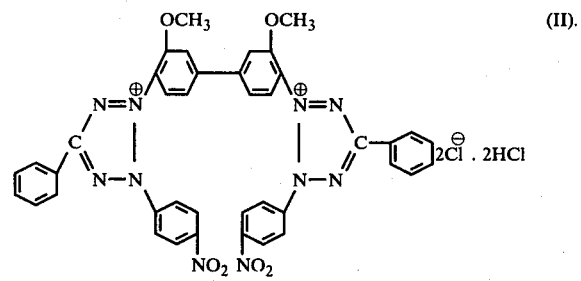

by oxidizing formazans having the general formula

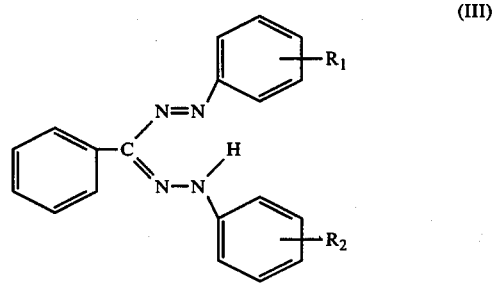

where $R_1$ and $R_2$ are as specified above, or formazan of the formula

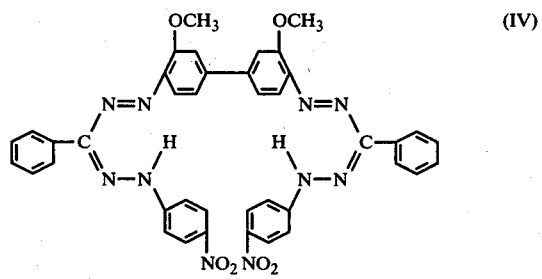

with chlorine, in a medium of a polar solvent, at a temperature of from −5° to +20° C.; chlorine is introduced into said solvent in the gaseous state, the molar ratio of formazan to chlorine being from 1:1 to 1:10; when the oxidation process has been completed, the end product is isolated.

The proposed method of oxidation of formazans precludes formation of resins or decomposition of a considerable portion of the product. For example, the yield of 2,3,5-triphenyltetrazolium chloride is as high as 80 percent. The time of the synthesis is reduced from 10 hours to 10–60-minutes.

In order to obtain the end product in crystal form, it is recommended that a solvent miscible with water be used as the polar organic solvent, and that the oxidation process be carried out in the presence of sodium hydrochloride taken in the quantity equimolar with respect to formazan.

To increase the yield of the end product to 90 percent (the assay being not less than 96 percent), it is recommended that absolute ethyl alcohol be used as the polar organic solvent.

In order to purify the obtained 2H-tetrazolium chloride hydrochloride from iron salts, and also to decrease the hydrogen chloride content of said salt, it is recommended to treat the obtained 2H-tetrazolium chloride hydrochloride with aqueous ammonia to pH 8 at the stage of isolation.

The proposed method makes it possible ot convert 2H-tetrazolium chloride hydrochloride, obtained in the process of oxidation, into 2H-tetrazolium chloride. To that end 2H-tetrazolium chloride hydrochloride is treated, at the stage of isolation, with potassium hydroxide solution in ethyl alcohol, the ratio of the alkali to the hydrochloride being equimolar.

According to the proposed method, the duration of the synthesis is reduced two or three times if the oxidation process is effected in a reactor, provided with a diffuser and a turbine agitator, made out of titanium, instead of glass as is the case with the laboratory equipment.

1,3,5-Triphenylformazan, 1-(4-nitrophenyl)-3,5,-diphenylformazan, 1-(2-carboxymethoxy-4-nitrophenyl)-3-phenyl-5-(2-carboxymethoxyphenyl)formazan, 1-(2-carboxymethoxyphenyl)-3-phenyl-5-(2-hydroxyphenyl)formazan, 1,3,-(diphenyl)-5-(chloro)-phenylformazan, dinitrodimethoxydiformazan, etc., can be used as the starting formazans in the proposed method.

The polar organic solvents that can be used in the proposed method are, e.g., methyl alcohol, ethyl alcohol, propyl alcohol, toluene, methyl acetate, or ethyl acetate.

The proposed method can be realized as follows.

Equimolar quantities of sodium hydroxide and formazan are mixed in absolute ethyl alcohol (the weight ratio of formazan to ethyl alcohol being from 1:15 to 1:25) with blowing gaseous chlorine blown through ethyl alcohol (the molar ratio of formazan to chlorine being from 1:2 to 1:5) at a temperature from −5° to +20° C. When the reaction mixture becomes colorless, the reaction is over. The end product is now isolated by any suitable method, e.g. by mixing the reaction mixture with activated carbon, filtering, evaporating the filtrate, extracting with water, and evaporating the aqueous extract to crystallize the end product, 2H-tetrazolium chloride hydrochloride.

For a better understanding of the invention the following examples of preparing 2H-tetrazolium chloride and 2H-tetrazolium chloride hydrochloride are given by way of illustration.

EXAMPLE 1

Preparing 2,3,5-triphenyltetrazolium chloride hydrochloride 5 g (0.015 M) of 1,3,5-triphenylformazan were dissolved in 100 ml of ethyl acetate in a round-bottomed flask with 1 liter (0.043 M) of chlorine gas blown through at a temperature of 0° C. for an hour. The reaction mixture was transferred into 1 liter of absolute diethyl ether. The amorphous product was re-precipitated several times from ethyl alcohol with diethyl ether, and dried in a vacuum desiccator. The yield of product was 4.2 g (70 percent). The assay was 96 percent.

Found, in percent: C, 60.20, 59.87, H, 4.70, 4.45; Cl, 16.46, 16.70, N, 14.65, 14.53. $C_{19}H_{15}N_4Cl.0.75HCl.H_2O$. Calculated, in percent: C, 60.00, H, 4.71, Cl, 16.30, N, 14.75.

EXAMPLE 2

Preparing 2,3,5-triphenyltetrazolium chloride hydrochloride 5 g (0.015 g (0.015 M) of 1,3,5-triphenylformazan were dissolved in 100 ml of absolute ethyl alcohol in a round-bottomed glass flask with thorough stirring of the mixture. 0.96 liter (0.042M) of chlorine gas was blown through at a temperature of 20° C. for 40 minutes until the red color vanished. The solution obtained was mixed with 0.5 g of activated carbon, then filtered and the filtrate added to 1 liter of diethyl ether to precipitate 4.5 g of amorphous 2,3,5-triphenyltetrazolium chloride hydrochloride. The yield was 75 percent.

The second half-wave potential, characterizing the reduction to formazan, $E_{1/2} = -0.7$ V.

Found, in percent: C, 60.20, 59.87; H, 4.70, 4.45; Cl, 16.46, 16.70; N, 14.65, 14.53. $C_{19}H_{15}N_4Cl.0.75HCl.H_2O$. Calculated, in percent: C, 60.00, H, 4.71, Cl, 16.30, N, 14.75.

At a temperature of 150°–165° C. the hydrochloride was split off, the process being accompanied by foaming of the powdered salt in a capillary. At a temperature of 227°–228° C. the powder melted with decomposition.

EXAMPLE 3

Preparing 2,3,5-triphenyltetrazolium chloride 2,3,5-triphenyltetrazolium chloride hydrochloride obtained in Example 2 was dissolved in ethyl alcohol and treated with a solution of potassium hydroxide in ethyl alcohol. The ratio of the alkali to the hydrochloride was equimolar. The solution was filtered, and the filtrate poured into diethyl ether. The product was separated on a filter. The obtained product melted at 230°–231° C. with decomposition. The second half-wave potential, at which the product was reduced to formazan, $E_{1/2} = -0.73$ V.

Found, in percent: C, 64.34, 64.15; H, 4.44, 4.33; Cl, 10.00, 10.04; N, 15.92, 15.80. $C_{19}H_{15}N_4Cl.H_2O$. Calculated, in percent: C, 64.40, H, 4.85, Cl, 10.04, N, 15.88.

EXAMPLE 4

Preparing 2,3,5-triphenyltetrazolium chloride trihydrochloride

The procedure is the same as in Example 2, except that the quantity of chlorine gas used was 3.5 liters (0.15 M). The yield of product was 5.0 g (69 percent).

Found, in percent: Cl, 32.15, 31.98. $C_{19}H_{15}N_4Cl.3HCl$. Calculated, in percent: Cl, 32.35.

As the product was recrystallized from dimethyl formamide, the hydrochloride was cleft off.

EXAMPLE 5

Preparing 2,3,5-triphenyltetrazolium chloride hydrochloride 5 g (0.015 M) of 1,3,5-triphenylformazan and 0.7 g (0.015 M) of sodium hydroxide were mixed in 100 ml of absolute ethyl alcohol and 0.96 liter (0.042 M) of chlorine gas was passed through for 45 minutes at a temperature of 05° C. Activated carbon was added, the components mixed, the mixture passed through a filter, the filtrate evaporated, the residue dissolved in water, treated with activated carbon, filtered, and the filtrate evaporated. The obtained crystals were white with a creamy tint. The yield of the end produce was 4.8 g (85 percent).

EXAMPLE 6

Preparing 2,3,5-triphenyltetrazolium chloride hydrochloride

The procedure is the same as in Example 5, except that the temperature of the reaction was $-1°$ C., the time during which chlorine gas was passed was 35 minutes, and methyl alcohol was used as the polar organic solvent. The yield of the end product was 4.8 g (85 percent). The assay was 92 percent.

EXAMPLE 7

Preparing 2,3,5-triphenyltetrazolium chloride hemihydrochloride 25 g (0.08 M) of 1,3,5-triphenylformazan, 550 ml of absolute ethyl alcohol, and 3.64 g (0.086 M) of sodium hydroxide were mixed in a glass flask provided with a glass stirrer and 4.8 liters (0.21 M) of chlorine gas passed through for 35 minutes at a temperature of $-1°$ C. Activated carbon was added to the reaction mixture containing 2,3,5-triphenyltetrazolium chloride hydrochloride ($n=0.75$), the mixture stirred and filtered, the filtrate evaporated, the residue extracted with water, the aqueous extract treated with activated carbon, and filtered. The filtrate was treated with aqueous ammonia to pH 8, then treated with activated carbon, filtered, and the filtrate evaporated. The yield of product was 86 percent. The assay of 2,3,5-triphenyltetrazolium chloride hemihydrochloride ($n=0.5$) was 96 percent. The crystalline product had a creamy tint.

EXAMPLE 8

Preparing 2,3,5-triphenyltetrazolium chloride hemihydrochloride.

The procedure is the same as in Example 7, except that a reactor with a diffuser and a turbine agitator, made of titanium, was used instead of the glass reaction flask and the glass stirrer. The oxidation continued for 18 minutes. The yield of crystalline product is 83 percent. The assay was 96 percent.

EXAMPLE 9

Preparing 2-(2-carboxymethoxyphenyl)-3-(2-carboxymethoxy-4-nitrophenyl)-5-phenyltetrazolium chloride hemihydrochloride 5 g (0.01 M) of 1-(2-carboxymethoxy-4-nitrophenyl)-3-phenyl 5-(2-carboxymethoxyphenyl)-formazan and 120 ml of absolute ethyl alcohol were mixed in a glass beaker and 1.2 liters (0.05 M) of chlorine gas was passed through at a temperature of 0° C. for 20 minutes. 0.5 g of activated carbon was added to the reaction mixture, mixed for 15 minutes, and filtered. The filtrate was transferred into 4 liters of diethyl ether, the precipitate separated and reprecipitated from ethyl alcohol with diethyl ether. The yield of product was 4.2 g (75 percent).

Found, in percent: C, 49.14, 48.70; H, 3.38, 3.37; Cl, 9.98, 9.72; N, 11.78, 12.0. $C_{23}H_{18}N_5O_8Cl.0.5HCl.H_2O$. Calculated, in percent: C, 48.98, H, 3.66, Cl, 9.43, N, 12.41.

EXAMPLE 10

Preparing 2,5-diphenyl-3-(4-nitrophenyl)-tetrazolium chloride hydrochloride 5 g (0.0.145 M) of 1-(4-nitrophenyl)-3,5-diphenyl-formazan 0.58 g (0.0145 M) of sodium hydroxide, and 100 ml of absolute ethyl alcohol were mixed in a glass beaker and 1 liter (0.043 M) of chlorine gas passed through at a temperature of 0° C. for an hour. The reaction mixture containing 2,5-dephenyl-3-(4-nitrophenyl)-tetrazolium chloride hydrochloride ($n=0.75$) was treated with activated carbon, filtered, the filtrate evaporated and the residue extracted with 100 ml of distilled water at a temperature of 70° C., the aqueous extract treated with activated carbon and filtered again. The filtrate was treated with aqueous ammonia to pH8. The solution was treated with activated carbon, filtered, and the filtrate evaporated. The crystalline precipitate was dried, the crystals ground and reprecipitated from absolute ethyl alcohol with diethyl ether. The yield of crystalline product was 4.4 g (80 percent). The assay was 98 percent. The product melted at 210–212° with decomposition.

Found, in percent: C, 56.44, 55.82; H, 3.88, 3.82; N, 17.6, 17.64; Cl, 11.4, 11.54. $C_{19}H_{14}N_5O_2Cl.0.25HCl.0.75H_2O$. Calculated, in percent: C, 56.5, H, 3.92, N, 17.4, Cl, 11.03.

EXAMPLE 11

Preparing 2-(2-hydroxyphenyl)-3-(2-carboxymethoxyphenyl)-5-phenyltetrazolium chloride hydrochoride 5 g (0.012 M) of 1-(2-carboxymethoxyphenyl)-5-phenyl-5-(2-hydroxyphenyl)-formazan was mixed in 100 ml of absolute ethyl alcohol and 0.9 liters (0.04 M) of chlorine gas was passed through at a temperature of $-5°$ C. for 10 minutes until the red color vanished. 0.5 g of activated carbon was added to the reaction mixture and stirred for 15 minutes. The carbon was separated by filtration, and 2-(2-hydroxyphenyl)-3-(2-carboxymethoxyphenyl)-5-phenyltetrazolium chloride hydrochoride was precipitated with ethyl ether. The yield was 5.4 g (96 percent). The product was reprecipitated from absolute ethyl alcohol with diethyl ether (1:6). The yield was 4 g (71 percent).

Found, in percent: C, 54.14, 54.65; H, 3.98, 3.98; N, 11.15 11.1; Cl, 10.2, 10.87. $C_{21}H_{16}N_4O_4.1.5HCl.0.5C_2H_5OH.H_2O$. Calculated, in percent: C, 54.59, H, 4.67, N, 11.56, Cl, 10.98.

The second half-wave potential at which reduction to formazan takes place was $E_{1/2} = -1.25$ V.

EXAMPLE 12

Preparing 2-(4-chloro)phenyl-3,5-diphenyltetrazolium chloride hydrochloride 3 g (0.01 M) of 1,3-(diphenyl)-5-(4-chloro)-phenyl-formazan was in 60 ml of absolute ethyl alcohol and 0.6 liters (0.03 M) of chlorine gas was passed through at a temperature of from $-2°$ to 0° C. for 10 minutes. 0.3 g of activated carbon was added and mixed for 15 minutes. The carbon was separated by filtration, and the product precipitated from the filtrate with diethyl ether then reprecipitated two times from absolute ethyl alcohol with diethyl ether. The yield of white powdered product was 2 g, which corresponds t 50%. The assay of 2-(4-chloro)-phenyl-3,5-diphenyl-tetrazolium chloride hydrochloride was 98 percent.

Found, in percent: C, 54.92; H, 3.80; N, 13.29; Cl, 23.70. $C_{19}H_{14}N_4Cl_2.0.75HCl.H_2O$ Calculated, in percent: C, 55.05; H, 4.06; N, 13.51; Cl 23.52.

EXAMPLE 13

Preparing 2,2'-di-(4-nitrophenyl)-5,5'-diphenyl-3,3'-dimethoxy-4,4'-diphenylene)-ditetrazolium chloride hydrochloride (nitrotetrazolium blue)

The experiment was carried out as described in Example 5, the difference being in that dinitrodimethoxydiformazan in an amount of 3.7 g (0.005 M) was used as the initial formazan. The end product was reprecipitated from ethanol by diethyl ether (1:10). The yield of the product was 3.7 g (90%). Slightly yellow crystals.

Found, in percent: N, 14.25; Cl, 14.70. $C_{40}H_{30}N_{10}O_6Cl_2\cdot 2HCl\cdot 4H_2O$. Calculated, in percent: N, 14.55, Cl, 14.74.

We claim:

1. In a method for preparing 2H-tetrazolium chloride and 2H-tetrazolium chloride hydrochloride having the general formula

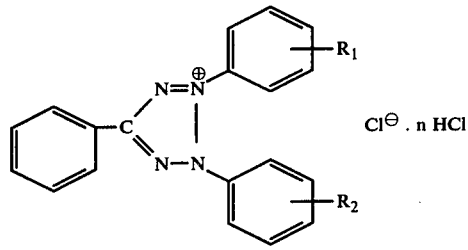

where $R_1$ and $R_2$ are H, OH, $NO_2$, Cl, or $OCH_2COOH$, and $n$ is from 0 to 3, and di-2H-tetrazolium chloride hydrochoride, having the formula

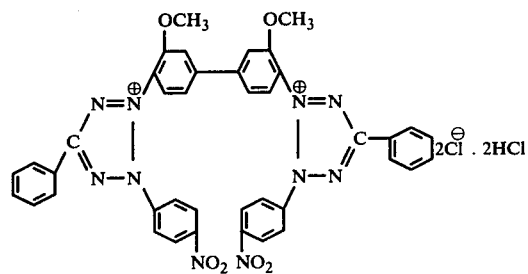

wherein formazans having the formula

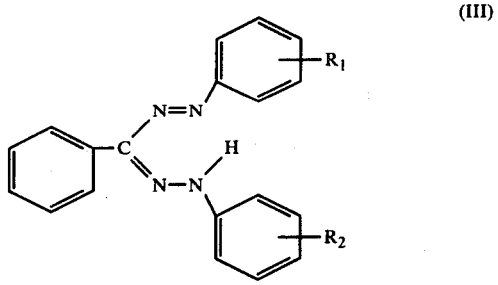

where $R_1$ and $R_2$ are as specified above, and respectively, having the formula

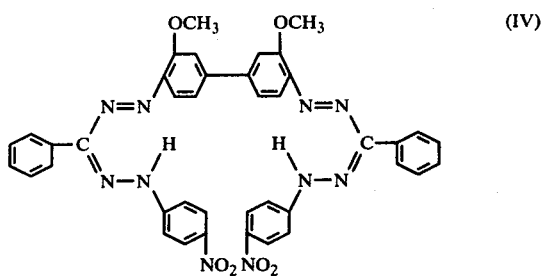

are oxidized, the improvements which comprise oxidizing with gaseous chlorine in a medium of a polar organic solvent at a temperature from $-5$ to $+20°$ C.; and a molar ratio of formazan to chlorine being from 1:1 to 1:10; when the oxidation process is over, the end product is isolated.

2. A method according to claim 1, in which a solvent miscible with water is used as the polar organic solvent, and the process of oxidation is carried out in the presence of an amount of sodium hydroxide equimolar with respect to the formazan.

3. A method according to claim 1, in which solvents selected from the group consisting of absolute ethyl alcohol, methyl alcohol, and ethyl acetate are used as the polar organic solvents.

4. A method according to claim 1, in which compounds selected from the group consisting of 1,3,5-triphenylformazan, 1-(4-nitrophenyl)-3,5-diphenylformazan, 1-(2-carboxymethoxy-4-nitrophenyl)-3-phenyl-5-(2-carboxymethoxyphenyl)-formazan, 1-(2-carboxymethoxyphenyl)-3-phenyl-5-(2-hydroxyphenyl)-formazan, 1,3-(diphenyl)-5-(4-chloro)phenyl-formazan, and dinitrodimethoxydiformazan are used as the formazans.

5. A method according to claim 1, in which the obtained 2H-tetrazolium chloride hydrochloride, at the stage of isolation, is treated with an aqueous ammonia to pH 8.

6. A method according to claim 1, in which the obtained 2H-tetrazolium chloride hydrochloride, at the stage of isolation, is converted into 2H-tetrazolium chloride by treating with potassium hydroxide solution in ethyl alcohol, the alkali to the hydrochloride ratio being equimolar.

* * * * *